United States Patent

Oguri et al.

[11] Patent Number: 6,002,792
[45] Date of Patent: Dec. 14, 1999

[54] SEMICONDUCTOR DEVICE INSPECTION SYSTEM

[75] Inventors: Shigehisa Oguri; Eiji Inuzuka; Kouji Suzuki; Wataru Nagata; Yasushi Hiruma, all of Hamamatsu, Japan

[73] Assignee: Hamamatsu Photonics KK, Hamamatsu, Japan

[21] Appl. No.: 08/607,873

[22] Filed: Feb. 29, 1996

Related U.S. Application Data

[62] Division of application No. 08/341,906, Nov. 15, 1994.

[30] Foreign Application Priority Data

Nov. 16, 1993 [JP] Japan .................................. 5-286820
Nov. 7, 1994 [JP] Japan .................................. 6-272519

[51] Int. Cl.$^6$ .......................... G06K 9/00; G01R 31/302
[52] U.S. Cl. .......................... 382/145; 382/149; 324/750
[58] Field of Search ................................ 382/145, 149; 324/750

[56] References Cited

U.S. PATENT DOCUMENTS

| 4,623,256 | 11/1986 | Ikenaga et al. | 356/394 |
|---|---|---|---|
| 4,644,404 | 2/1987 | Tabei | 348/304 |
| 4,712,057 | 12/1987 | Pan | 250/310 |
| 4,755,874 | 7/1988 | Esrig et al. | 382/149 |
| 4,792,682 | 12/1988 | Endou et al. | 250/338.3 |
| 5,006,717 | 4/1991 | Tsutsu et al. | 250/484.2 |
| 5,040,228 | 8/1991 | Bose et al. | 382/141 |
| 5,126,569 | 6/1992 | Carlson | 250/341.4 |
| 5,126,718 | 6/1992 | Doctor | 340/567 |
| 5,136,373 | 8/1992 | Kamiya et al. | 348/92 |

(List continued on next page.)

FOREIGN PATENT DOCUMENTS

| 0149849 | 7/1985 | European Pat. Off. . |
|---|---|---|
| 0179309 | 4/1986 | European Pat. Off. . |
| 0242045 | 10/1987 | European Pat. Off. . |
| 0418918 | 3/1991 | European Pat. Off. . |
| 0 635 883 A2 | 1/1995 | European Pat. Off. . |
| 4-1560 | 1/1992 | Japan . |
| 5129401 | 5/1993 | Japan . |

OTHER PUBLICATIONS

"Failure Analysis of Multilevel Metalized LSI Usingoptical Beam Induced Current" J. Mitsuhashi et al 94.7.11, pp. 711–714.

"Quantitative Emission Microscopy", 94.7.11, J. Kolzer et al, pp. R23–R41.

Paragraph 4 Hot Electron Analyzer, Eiji Inuzuka, Hamamatsu Photonics Co. Ltd. 94.9.29, pp. 319–325.

(List continued on next page.)

Primary Examiner—Phuoc Tran
Assistant Examiner—Daniel G. Mariam
Attorney, Agent, or Firm—Pillsbury Madison & Sutro LLP

[57] ABSTRACT

The present invention relates to an inspection system for transparently taking an image of inside of a semiconductor device to analyze anomalous occurrence. First, image data obtained under infrared ray illumination are converted into a first left-to-right reversed image data in which the obtained image data are reversed left to right and the first left-to-right reversed image data are stored. Next, very weak light emitted from an anomalous portion when the semiconductor device is biased is picked up under no illumination. Then, image data of very weak light is converted into a second left-to-right reversed image data in which the image data of weak light are reversed left to right. The first and second left-to-right image data are superimposed to superimpose the image specifying the anomalous location on an image of chip patterns in the semiconductor device and the superimposed image is displayed. Further, in the infrared-ray epi-irradiation means, an optical filter made of the same material as that of the semiconductor device to be measured is used to form infrared rays for illumination, so that when the back surface of the semiconductor device is irradiated with infrared rays produced by the optical filter, light having a short wavelength which is easily reflected on the surface of the semiconductor device is interrupted and infrared rays having high transmittance against the semiconductor device can be obtined.

13 Claims, 5 Drawing Sheets

U.S. PATENT DOCUMENTS

| | | | |
|---|---|---|---|
| 5,208,648 | 5/1993 | Batchelder et al. | 356/237 |
| 5,396,068 | 3/1995 | Bethea | 250/330 |
| 5,410,400 | 4/1995 | Shishido et al. | 356/237 |
| 5,463,494 | 10/1995 | Hobrock | 359/359 |
| 5,486,919 | 1/1996 | Tsuji et al. | 356/349 |
| 5,488,305 | 1/1996 | Bloom et al. | 324/750 |
| 5,493,236 | 2/1996 | Ishii et al. | 324/750 |
| 5,548,211 | 8/1996 | Tujde et al. | 324/750 |
| 5,598,100 | 1/1997 | Maeda et al. | 324/750 |

OTHER PUBLICATIONS

Patent Abstracts of Japan, vol. 11, No. 117 (E–498), Apr. 11, 1987 & JP–A–61 263235 (NEC) Jun. 7, 1988.

Patent Abstracts of Japan, vol. 12, No. 394 (P–77) Oct. 20, 1988 & JP–A–63 134943 (NEC) Jun. 7, 1988.

Patent Abstracts of Japan, vol. 13, No. 350 (E–800) Aug. 7, 1989 & JP–A–01 109735 (Fujitsu) Apr. 26, 1989.

Patent Abstracts of Japan, vol. 12, No. 130 (E–603) Apr. 21, 1988 & JP–A–62 257739 (Toshiba) Nov. 10, 1987.

SEMICONDUCTOR DEVICE INSPECTION SYSTEM

This is a division of application Ser. No. 8/341,906, filed Nov. 15, 1994.

BACKGROUND OF THE INVENTION

1. Field of the Invention

The present invention relates to a semiconductor device inspection system for analyzing anomalous occurrences inside a semiconductor device and for evaluating reliability of a semiconductor device, and more particularly to a semiconductor device inspection system for transparently taking an image of inside of a semiconductor device.

2. Related Background Art

As a semiconductor device is highly integrated, e.g., VLSI, difficulty of anomaly analysis and reliability evaluation of internal circuits of the semiconductor device is increased.

In such present condition, much attention is focused on the analysis technology to track down the location of an anomalous portion by detecting very weak light emitted from the anomalous portion in semiconductor device. An emission microscope is known as a semiconductor device inspection apparatus utilizing such analysis technology.

The emission microscope picks up very weak light caused by hot carriers, which are produced when an electric field is concentrated on an anomalous portion in semiconductor device, or very weak light in the infrared region caused by latchup. Therefore, the emission microscope can measure a semiconductor device to be checked without contact and with high accuracy.

However, the emission microscope has such a problem that since it detects emitted light in the visible to infrared region, it could become incapable of measuring emitted light if there would exist some shielding object between an anomalous portion emitting very weak light and the emission microscope.

In particular, in order to make a semiconductor device being highly integrated, semiconductor devices tend to employ the chip structure in which interconnection between numerous elements such as transistors is made by multilayer wiring located on the top surface. The multilayer wiring interrupts the very weak light caused by an anomaly of an element underneath the multilayer wiring, which caused a problem of inability of measurement or not permitting high-accuracy measurement. In semiconductor devices to which the so-called Lead On Chip packaging structure is applied, a lead frame covers the top surface of the semiconductor chip. For such devices, similarly to the case of the multilayer wiring, the lead frame will be a shielding object and interrupt the very weak light, resulting in inability of measurement or not permitting high-accuracy measurement.

Further, there is another problem in applications of the emission microscope. For example, it is known as an observing method that a top surface of a plastic mold is chemically removed, e.g., by fuming nitric acid to expose the surface of semiconductor chip and when a predetermined bias power source is connected to a lead frame to supply power to internal circuits of the semiconductor chip, very weak light is emitted from an anomalous portion, which is observed from the top surface of the semiconductor chip. However, when the plastic mold is chemically removed, e.g., by fuming nitric acid, the circuit patterns or others inside the semiconductor chip could be damaged, which could hinder observation of an anomalous portion to be observed originally.

To solve these problems of emission microscopes, a semiconductor device inspection system (Japanese Patent Application No. HEI 5-177957 (177957/1993)) was developed. This inspection system is to illuminate the back surface of a semiconductor device, that is, the back surface where shielding objects such as multilayer wiring of the semiconductor chip are not formed, by an infrared-ray epi-illumination means and to take an optical image reflected and transmitted through the semiconductor chip. Therefore, an observed image specifying an anomalous location in the semiconductor chip can be obtained. However, even with this semiconductor device inspection system, still there were problems to be solved, e.g., large noise components, in order to obtain a clearer image.

SUMMARY OF THE INVENTION

It is an object of the present invention to provide a semiconductor device inspection system capable of obtaining a clearer image than in the prior art. In order to achieve the above object, the present invention comprises infrared-ray epi-illumination means, image pickup means, image reversing means, adding means, and superimposed display control means.

The infrared-ray epi-illumination means makes light in a wide region of wavelengths including an infrared region emitted from a light source pass through an optical filter made of the same material as that of the semiconductor device to form an infrared ray and irradiates the back surface of the semiconductor device with the infrared ray.

The image pickup means picks up an image transmitted from inside the semiconductor device when the back surface of the semiconductor device is irradiated with the infrared ray, and further detects (picks up) very weak light generated inside the semiconductor device under no illumination.

The image reversing means produces left-to-right reversed first image data by left-to-right-reversing an array of pixels in image data output when the image pickup means picks up the image of the bottom surface of the semiconductor device under illumination by the infrared-ray epi-illumination means and produces second left-to-right-reversed image data by left-to-right-reversing an array of Dixels in image data output when the image pickup means picks up an image of very weak light emitted from an anomalous portion in the semiconductor device under no illumination.

The adding means superimposes the first left-to-right-reversed image data and the second left-to-right-reversed image data generated by the image reversing means with correspondence of pixel array elements and, outputs superimposed data.

The superimposed display control means makes display means display a restored image, based on the superimposed data output from the adding means.

In the infrared ray semiconductor device inspection system of the present invention having the above-described structure, an image of the semiconductor device to be measured is taken from the bottom and an image of very weak light from the anomalous occurring portion and a pattern image are taken and displayed as a superimposed observed image as if it is observed from the top. Therefore, even though there exists a shielding object such as aluminum wiring, which interrupts light, on the top surface, the anomalous occurring location can be specified with high accuracy. Further, the image of very weak light is converted into the image observed from the top in real time and displayed, so that anomalous occurrence can be analyzed for short period of time.

In particular, in the infrared-ray epi-irradiation means, an optical filter made of the same material as that of the semiconductor device to be measured is used to form infrared rays for illumination, so that light having a short wavelength which is easily reflected on the surface of the semiconductor device is interrupted and infrared rays having high transmittance against the semiconductor device can be obtained. In result, an image of reflected and transmitted infrared rays is picked up and an image of a noise component reflected at the surface of the semiconductor device is significantly suppressed. Therefore, a clear image which has less noise component and offset component can be obtained.

For example, to measure a semiconductor device made of silicon semiconductor, a silicon filter made of the same material as that of the semiconductor device is used as an optical filter. Then, the absorption wavelength limit of the silicon filter is a wavelength (about 1100 nm) equivalent to the energy band gap (about 1.1 ev) of silicon. Accordingly, light having a wavelength shorter than the absorption wavelength limit is removed and infrared rays having a wavelength longer than the absorption wavelength limit irradiate the semiconductor device. The wavelength region of the infrared ray matches with the transmittance sensitive region of the semiconductor device. Consequently, an image can be picked up with high sensitivity.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

One embodiment of an infrared-ray semiconductor device inspection system according to the present invention will be explained with reference to the drawings. First, referring to FIG. 1, the whole structure of the embodiment will be explained. The semiconductor device inspection system comprises an observation section A including a dark room box 1, a control section B for controlling a cooled CCD camera 2 and other components installed in the dark room box, and an analysis section C for receiving an image signal output from the cooled CCD camera 2 through the control section B and performing predetermined image processing.

Figure 1:
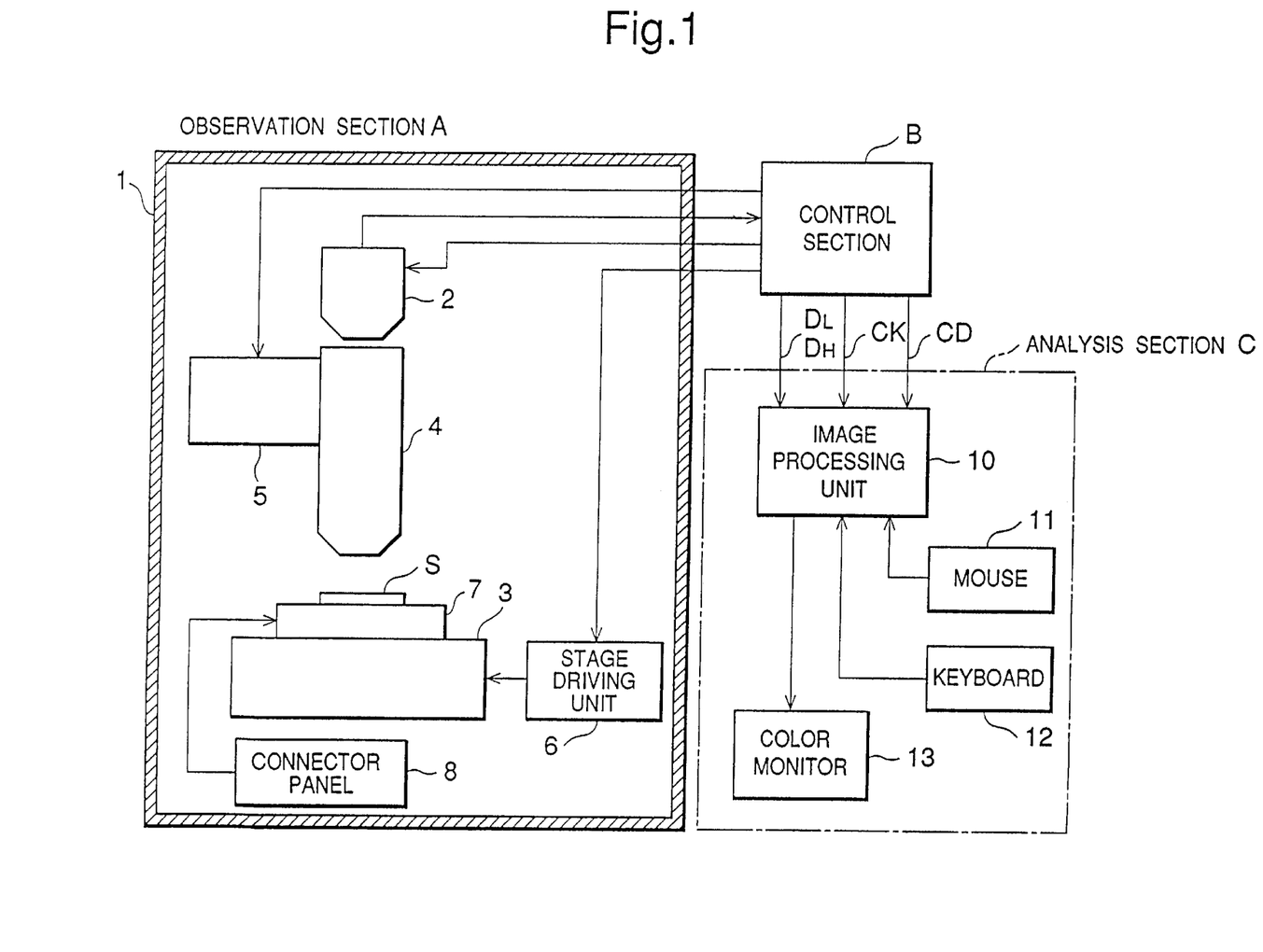
FIG. 1 is a block diagram showing the whole structure of one embodiment of a semiconductor device inspection system according to the present invention.

The dark room box 1 for intercepting incidence of external light contains a motor-driven XYZ stage 3 for carrying a semiconductor device S to be measured thereon and moving it in the X,Y,Z coordinate directions to position the semiconductor device S, an image pickup optical system 4 provided opposing to the motor-driven XYZ stage 3, for magnifying an image from the semiconductor device S by an arbitrary magnification within a predetermined range, a cooled CCD camera 2 for taking an image passing through the image pickup optical system 4, an infrared-ray epi-illumination device 5 for irradiating the semiconductor device S with infrared rays through the image pickup optical system 4, a stage driving unit 6 for controlling operations of the motor-driven XYZ stage 3 by supplying power, a test fixture 7 for supplying power to the semiconductor device S to make it operate and supplying a control signal, and a connector panel 8 for commanding the test fixture 7 to supply a control signal or others.

Figure 2:
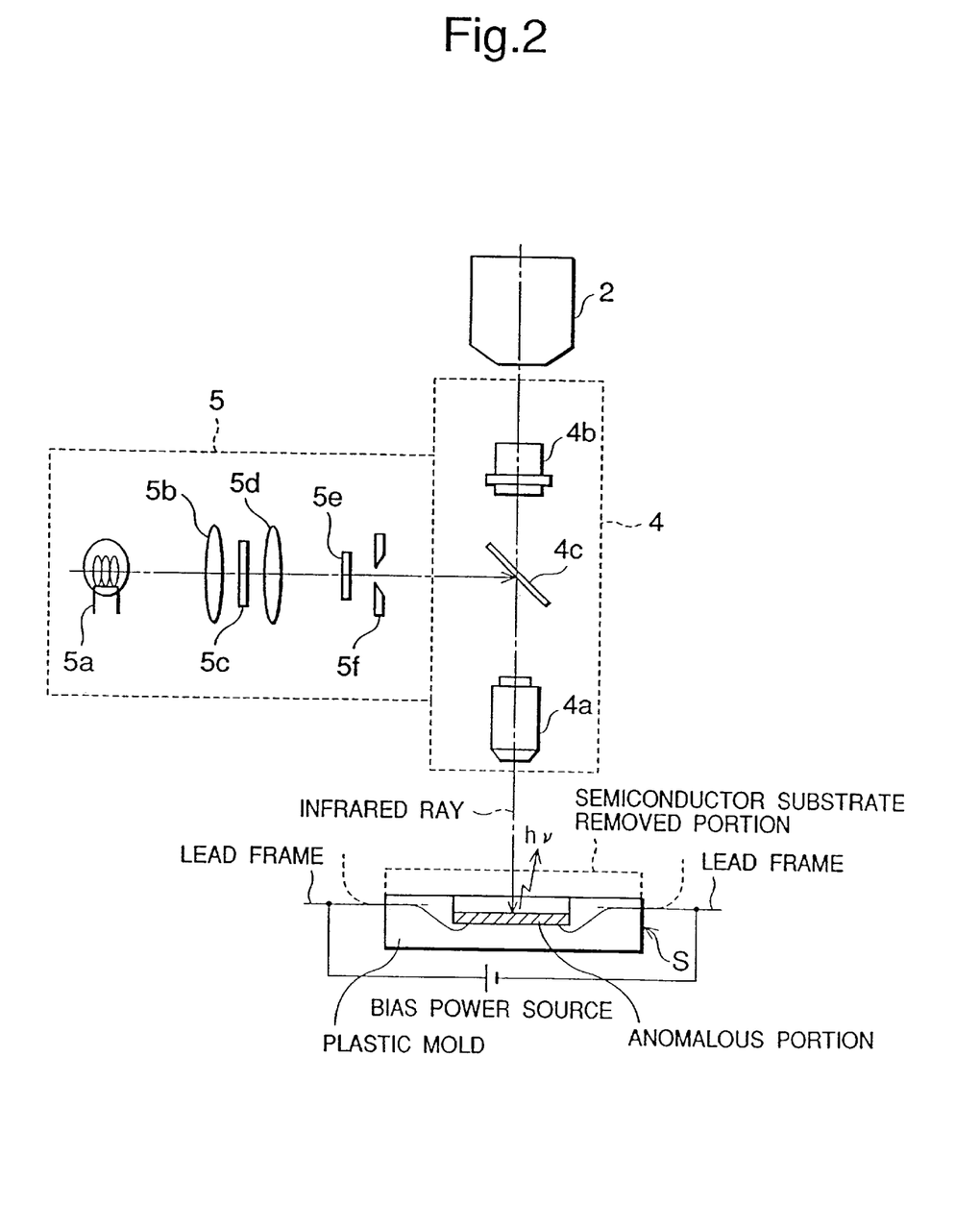
FIG. 2 is a block diagram showing the detailed structure of an image pickup optical system and an infrared-ray epi-irradiation device of one embodiment.

Next, referring to FIG. 2, the detailed structure of the image pickup optical system 4 and the infrared-ray epi-illumination device 5 will be described. The image pickup optical system 4 comprises an objective lens system 4a capable of magnifying an image from the semiconductor device S by an arbitrary magnification within a predetermined range, an image forming tens system 4b for forming an image magnified by the objective lens system 4a on a light receiving surface of the cooled CCD camera 2, and a half mirror 4c located between the objective lens system 4a and the image forming lens system 4b. Optical axes of the objective lens system 4a, the half mirror 4c and the image forming lens system 4b are matched with a normal of the light receiving surface of the cooled CCD camera 2. Note that the half mirror 4c transmits an image from the objective lens system 4a to the image forming lens system 4b and reflects infrared rays for illumination from the infrared-ray epi-illumination device 5 towards the objective lens system 4a.

The infrared-ray epi-illumination device 5 comprises a halogen lamp 5a which is a light source, and a condenser lens 5b, a transparent optical filter 5c, a condenser lens 5d, a diffusing plate 5e, and a field stop 5f, which are for forming infrared rays for illumination from light emitted from the halogen lump 5a and emitting infrared rays to the half mirror 4c and which are placed along the same optical axis. In particular, light emitted from the halogen lump 5a becomes parallel beams by the condenser lens 5b, and only infrared rays having a wavelength longer than a predetermined wavelength among parallel beams transmit through the optical filter 5c and the infrared rays are collected to a focal point by the condenser lens 5d. The diffusing plate 5e is placed at a focal point of the condenser lens 5d, and converts the collected infrared rays uniformly. Further, the field stop 5f reduces the uniform infrared rays into a predetermined beam, and emits it to the half mirror 4c.

In this embodiment, the optical filter 5c is a transparent optical filter made of the same material as that of the semiconductor device S to be measured since the semiconductor device S is made of silicon semiconductor.

Then, the infrared ray exited from the field stop 5f is reflected by the half mirror 4c, and transmits the objective lens 4a and then irradiates the semiconductor device S.

Figure 3:
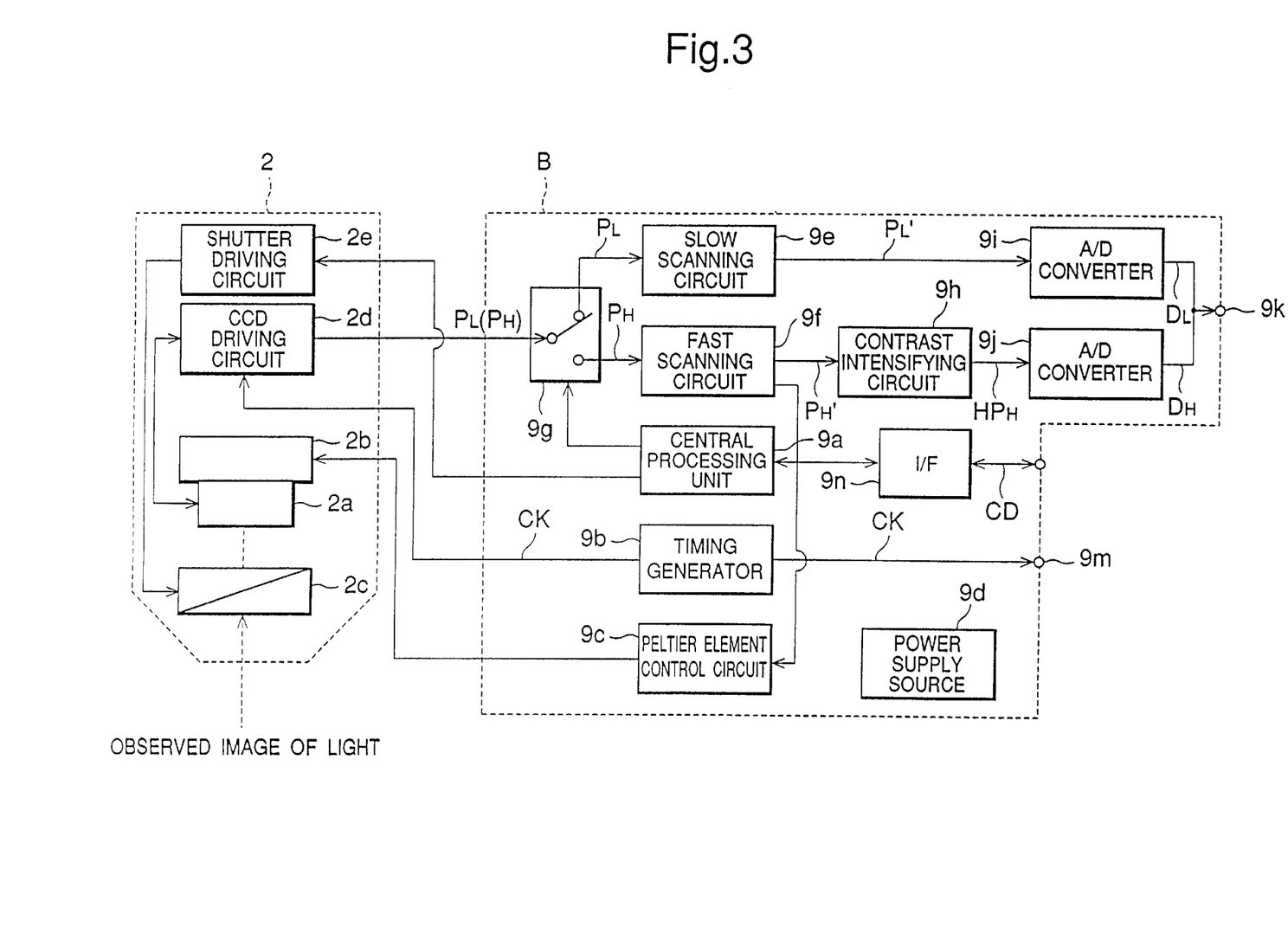
FIG. 3 is a block diagram showing the detailed structure of a cooled CCD camera and a control section of one embodiment.

Next, referring to FIG. 3, the structure of the cooled CCD camera 2 and the control section B will be explained. First, the cooled CCD camera 2 comprises a CCD solid state image sensor 2a having 1000×1018 pixels and a Peltier element 2b fixed in the CCD solid state image sensor. The CCD solid state image sensor 2a and the Peltier element 2b are placed in vacuum atmosphere which is set in vacuum by a vacuum pump (not shown) all the time. A shutter device 2c is placed in front of the light receiving surface (matched with the surface on which the image is formed by the image forming lens system 4b) of the CCD solid state image sensor 2a. Then, a CCD driving circuit 2d controls image pickup operations of the CCD solid state image sensor 2a, synchronizing with a synchronizing signal CK supplied from a timing generator 9b in the control section B. Further, a shutter driving circuit 2e controls opening and closing operations of the shutter device 2c based on instruction from a central processing unit 9a having a microprocessor. Furthermore, the Peltier element 2b is driven by current supplied from a Peltier element control circuit 9c in the control section to cool the CCD solid state image sensor 2a at a fixed temperature all the time thereby to suppress dark current generation and noise generation due to heat in the whole cooled CCD camera 2. The cooled CCD camera 2 is able to switch a slow pickup mode in which images are picked up for a long period of time and a signal $P_L$ for each pixel is read out from the CCD solid state image sensor 2a at point sequential timing of low frequency, and a fast pickup mode in which images are picked up ror a short period of time as compared with the slow pickup mode and a signal $P_H$ for each pixel is read out from the CCD solid state image sensor 2a at point sequential timing of high frequency. In the slow pickup mode, one frame cycle (cycle for reading out all image signals for pixels of one still image) is set to 4 seconds and in the fast pickup mode, it is set to 0.125 seconds.

The control section B comprises a central processing unit 9a for controlling whole operations of the observation section A and the control section B, a timing generator 9b for generating a synchronizing signal CK to set image pickup timing in the slow pickup mode and the fast pickup mode through the CCD driving circuit 2d, a Peltier element control circuit 9c for controlling temperature of the Peltier element 2b, and a power supply source 9d for supplying power required for whole operations of the observation section A and the control section B.

Further, the control section B comprises a slow scanning circuit 9e for holding and sampling an image signal $P_L$ for each pixel, which is read out from the CCD solid state image sensor 2a at Dredetermined point sequential timing (reading timing for one pixel, hereinafter called slow point sequential timing) in the slow pickup mode in synchronization with the slow point sequential timing, a fast scanning circuit 9f for holding and sampling an image signal $P_H$ for each pixel, which is read out from the CCD solid state image sensor 2a at predetermined point sequential timing (reading timing for one pixel, hereinafter called fast point sequential timing) in the fast pickup mode in synchronization with the fast point sequential timing, and a changeover circuit 9g for switching the image pickup modes to transmit the respective image signals $P_L$ and $P_H$ read out from the CCD solid state image sensor 2a to the slow scanning circuit 9e and the fast scanning circuit 9f.

Further, a contrast intensifying circuit 9h removes unnecessary signal components from the image signal $P_H'$ output from the Last scanning circuit 9f in the fast pickup mode, and thereafter amplifies the signal by a predetermined gain to form an image signal $HP_H$ with high contrast. In other words, the contrast intensifying circuit 9h removes a noise component and an offset component the amplitude of which are lower than threshold voltage $V_{TH}$ from the signal $P_H'$ output from the fast scanning circuit 9e, which leaves a real image signal $HP_H$. Thereafter, the contrast intensifying circuit 9h amplifies the signal $HP_H$, and then outputs the image signal $HP_H$ with high contrast. Note that the threshold voltage $V_{TH}$ can be arbitrarily adjusted by an observer.

Next, an A/D converter 9i converts an analog image signal $P_L'$ output from the slow scanning circuit 9e into digital image data $D_L$ in the slow pickup mode. On the contrary, an A/D converter 9j converts an analog signal $HP_H$ output from the contrast intensifying circuit 9h into digital image data $D_H$ in the fast pickup mode.

Then these image data $D_L$ and $D_H$ are transmitted to the analysis section C through a common output terminal 9k.

Since the sample hold timing of the slow scanning circuit 9e and the fast scanning circuit 9f synchronizes with a synchronizing signal CK from the timing generator 9b, the sample hold timing also synchronizes with the point secuential reading timing of the CCD solid state image sensor 2a in the slow pickup mode and the fast pickup mode. In order to assure transmittance of image data $D_L$ and $D_H$ to the analysis section C, the synchronizing signal CK is supplied to the analysis section C through the synchronizing signal output terminal 9m, and various kinds of control data CD are transmitted between the central processing unit 9a and the analysis section C through an interface circuit 9n which is in conformity with the RS232C standard.

Figure 4:
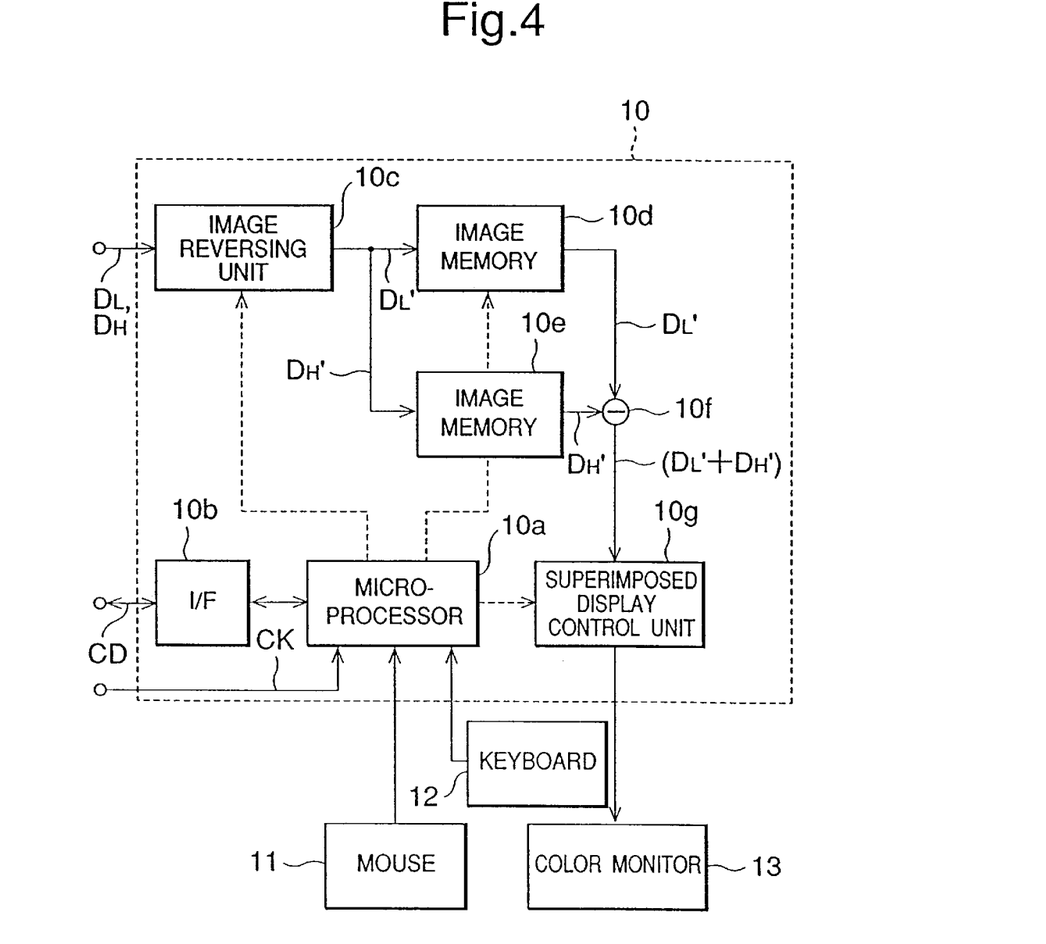
FIG. 4 is a block diagram showing the detailed structure of an analysis section of one embodiment.

Next, referring to FIG. 1 and FIG. 4, the structure of the analysis section C will be explained.

First, in FIG. 1, the analysis section C comprises an image processing unit 10 including a microprocessor 10a having various kinds of arithmetic functions, and a mouse input device 11, a keyboard input device 12 and a color monitor device 13 which are attached to the image processing unit 10. The image processing unit 10 receives image data $D_L$ and $D_H$ transmitted from the control unit 9 and receives and transmits various kinds of control data CD from and to the central processing unit 9a through an interface circuit 10b connected to an interface circuit 9n in the control section B in accordance with the RS232C standard. Further, the image processing unit 10 receives the synchronizing signal CK from the timing generator 9d.

The internal structure of the image processing unit 10 will be explained. The image processing unit comprises an image reversing unit 10c for changing the arrangement of the image data $D_L$ (or $D_H$) of a predetermined number of pixels transmitted from the control unit B to produce left-to-right-reversed image data $D_L'$ (or $D_H'$) for obtaining a left-to-right-reversed, reproduced image, an image memory 10d for storing left-to-right-reversed image data $D_L'$ of one frame from the image reversing unit 10c in the slow pickup mode, an image memory 10e for storing left-to-right-reversed image data $D_H'$ of one frame from the image reversing unit 10c in the fast pickup mode, an adding circuit 10f for adding the left-to-right-reversed image data $D_L'$ and $D_H'$ read out from the image memories 10d and 10e pixel by pixel to output the added image data ($D_L'+D_H'$), and an superimposed display control unit 10g for converting the added image data ($D_L'+D_H'$) output from the adding circuit 10f into video signal $V_D$ of video rate for each pixel to supply it to the color monitor 13.

Figure 5:
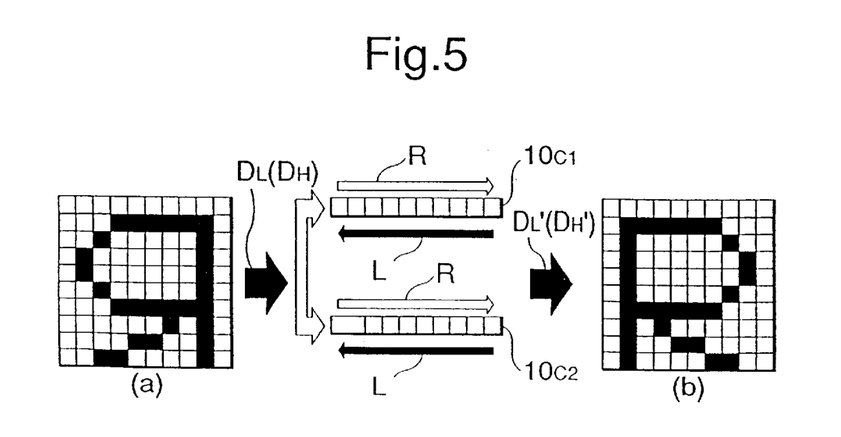
FIG. 5 is a view illustrating the structure of an image reversing unit in an analysis section and its function.

The image reversing unit 10c, as shown in FIG. 5, includes one pair of line buffers $10_{C1}$ and $10_{C2}$ for storing and outputting image data $D_L$ (or $D_H$) transmitted from the control section B in one horizontal line basis (in this embodiment, 1018 pixels). The input timing of each image data $D_L$ (or $D_H$) and the output timing of each left-to-right-reversed image data $D_L$ (or $D_H$) synchronizes with the slow point sequential timing in the slow pickup mode, and synchronizes with fast point sequential timing in the fast pickup mode. In other words, the line buffers $10_{C1}$ and $10_{C2}$ operate synchronizing with the synchronizing signal CK to convert the arrangement of image data $D_L$ into left-to-right-reversed image data $D_L'$ synchronizing with slow sequential timing in the slow pickup mode, and to convert the arrangement of image data $D_H$ into left-to-right-reversed image data $D_H'$ synchronizing with fast sequential timing in the fast sequential timing. Further, the line buffers $10_{C1}$ and $10_{C2}$ input image data $D_L$ (or $D_H$) by successively shifting data in a direction shown by the arrow R in FIG. 5 in synchronization with the point sequential reading timing and store image data $D_L$ (or $D_H$) of one horizontal line when the line buffers input image data $D_L$ (or $D_H$). Conversely, the line buffers $10_{C1}$ and $10_{C2}$ output the temporary stored image data $D_L$ (or $D_H$) in the reverse order to that upon input by successively shifting data in a direction shown by the arrow L in FIG. 5 when the buffers output data. Accordingly, thus outputted image data $D_L'$ (or $D_H'$) are left-to-right-reversed image data, which are reversed left to right with respect to the pixel order in the image data $D_L$ (or $D_H$).

Further, in synchronization with the above one horizontal reading cycle, one line buffer $10_{C1}$ is in input operation while the other line buffer $10_{C2}$ is in output operation. The operations of line buffers are switched by turns in synchronization with the above one horizontal reading cycle. Accordingly, while the line buffer $10_{C1}$ is in input operation to store image data $D_L$ (or $D_H$) of one horizontal line, the other line buffer $10_{C2}$ outputs the image data $D_L$ (or $D_H$) having been stored in the previous one horizontal reading cycle in the direction shown by the arrow L so as to output the left-to-right-reversed image data $D_L'$ (or $D_H'$) to the image memory $10d$ (or $10e$). Conversely, while the line buffer $10_{C2}$ is in input operation to store image data $D_L$ (or $D_H$) of one horizontal line, the other line buffer $10_{C1}$ outputs the image data $D_L$ (or $D_H$) having been stored in the previous one horizontal reading cycle in the direction shown by the arrow L so as to output the left-to-right-reversed image data $D_L'$ (or $D_R'$) to the image memory $10d$ (or $10e$). Such left-to-right-reversing process is repeated as the operations are switched every one horizontal reading cycle, so that, for example, the image data $D_L$ (or $D_H$) as shown in (a) of FIG. 5 are converted into the left-to-right-reversed image data $D_L'$ (or $D_R'$) as shown in (b) of FIG. 5. Then, such left-to-right-reversing process is carried out in real time in synchronization with the one horizontal reading cycle of the CCD solid state image sensor $2a$ and the timing of point sequential scan reading in the pixel-by-pixel basis.

Further, the mouse input device 11 and the keyboard input device 12 function as input devices when an operator gives an instruction to start measurement, adjusts the threshold voltage $V_{TH}$, and controls the operations of another systems.

Next, the operation of the semiconductor inspection system having such structure will be described, referring to the flowchart shown in FIG. 6.

Figure 6:
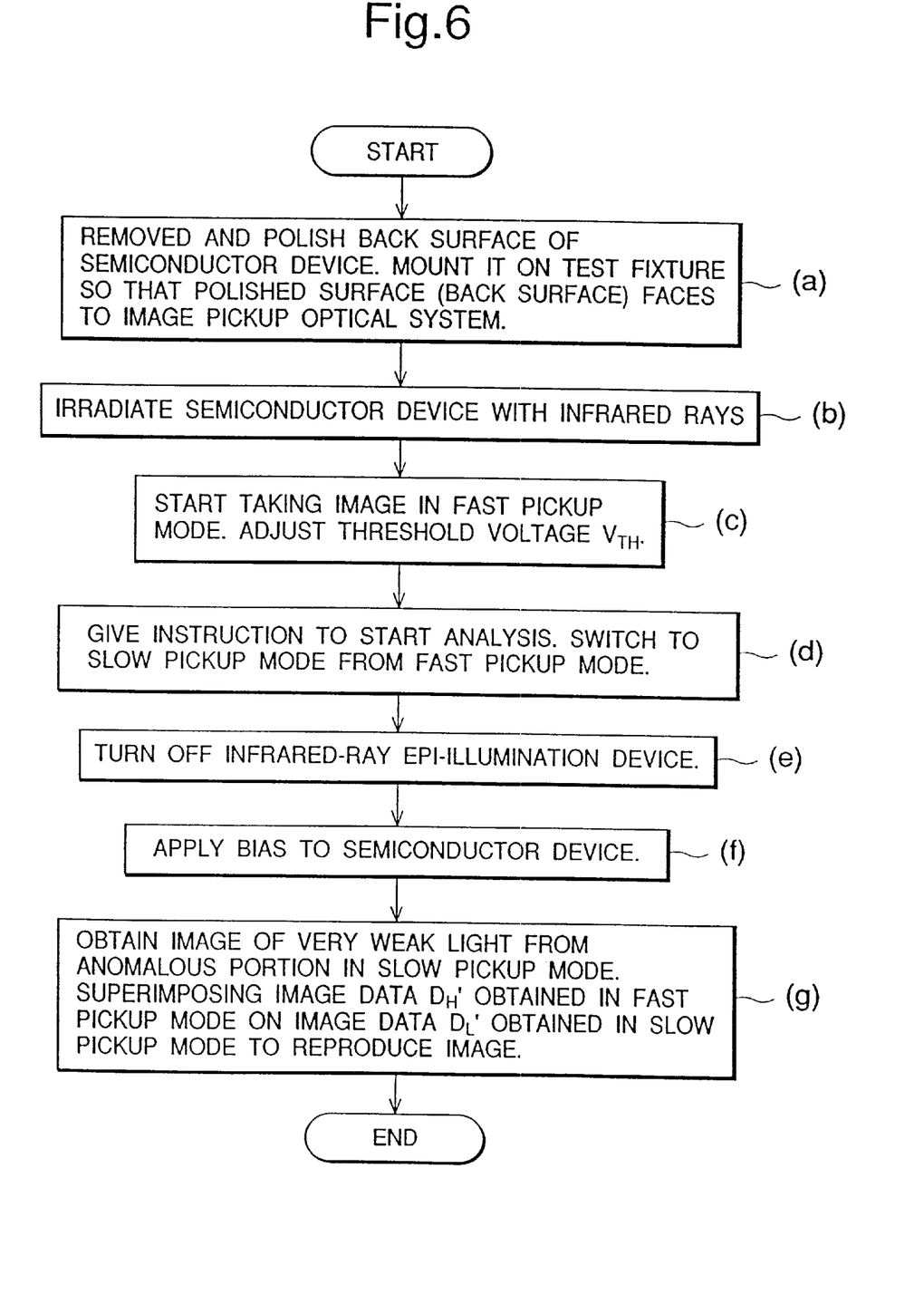
FIG. 6 is a flowchart to explain the operation of one embodiment.

First, in Step (a) of FIG. 6, a measuring person removes the bottom portion of mold package of semiconductor device S and polishes to obtain a mirror-finished surface of substrate of semiconductor chip and sets the semiconductor device S on the test fixture 7 such that the back surface is opposed to the objective lens system $4a$.

Next, in Step (b), the measuring person manipulates the mouse input device 11 or the keyboard input device 12 to illuminate the semiconductor device S by the infrared-ray epi-illumination device 5.

Then in Step (c), as the cooled CCD camera 2 is set to the fast pickup mode, the central processing unit $9a$ sets one frame cycle to 0.125 seconds and gives a predetermined period within the one frame cycle to the shutter driving circuit $2e$ as the exposure period. Next, the shutter device $2c$ repeats opening and closing for exposure and the CCD solid state image sensor $2a$ repeats taking image until the fast pickup mode is terminated, which will be described later. Accordingly, the color monitor 13 displays still picture every 0.125 seconds successively.

The image taking operation in one frame cycle will be described. As shown in FIG. 2, an infrared ray irradiating the back surface of semiconductor device S passes through the semiconductor substrate of semiconductor chip and light reflected on the surface of the semiconductor chip is incident on the image pickup optical system 4. Then during a predetermined exposure period, the shutter device $2c$ remains open, so that the cooled CCD camera 2 takes a reflected image.

That is, the cooled CCD camera 2 takes an image, e.g., of circuit patterns formed on the front surface of semiconductor chip from the back surface. After the predetermined exposure period elapses, the CCD solid state image sensor $2a$ outputs each image signal $P_H$, synchronizing with the fast point sequential timing. The fast scanning circuit $9f$ samples each image signal $P_H$ through the changeover circuit $9g$, and the contrast intensifying circuit $9h$ removes a noise component and an offset components from the image signal $P_H$. Further, the A/D converter $9j$ converts the image signal $P_H$ into digital image data $D_H$.

Here, one significant point is that when the semiconductor device S in which the substrate (chip) is made of silicon semiconductor is observed, the transparent optical filter $5c$ is a silicon filter made of the same material as that of the semiconductor device S, which makes the high sensitive image taking possible. In particular, because absorption wavelength limit of the silicon filter $5c$ is a wavelength (about 1100 nm) equivalent to energy band gap (about 1.1 eV) of silicon, light having a wavelength shorter than the absorption wavelength limit is removed and infrared rays having a wavelength longer than the absorption wavelength limit are used for illumination. On the other hand, energy band gap of silicon semiconductor substrate of semiconductor device S is also about 1.1 eV. Accordingly, the silicon semiconductor substrate is superior in transmittance of infrared rays having a wavelength longer than about 1100 nm. Infrared rays for illumination generated by means of silicon filter $5c$ have spectra of long wavelength which exactly match with a transmittance property of the silicon semiconductor, so that an image can be picked up with high sensitivity. Infrared rays for illumination have optimum transmittance to the silicon semiconductor after light having a wavelength shorter than a wavelength of about 1100 nm is removed, which lowers light to be reflected at the polished surface (back surface) of substrate. Then, almost all of images of reflected light are due to light transmitted and reflected inside the substrate of the semiconductor chip. Therefore, an image of reflected light has a very few noise and offset components, and circuit patterns formed in the semiconductor chip can be picked up clearly from the back surface.

Thus obtained image data $D_H$ are converted into left-to-right-reversed image data $D_H'$ in which the arrangement is reversed left to right by the image reversing unit 10c and temporary stored in the image memory 10e. Further, the left-to-right-reversed image data $D_H'$ is read out from the image memory 10e in real time and displayed on the color monitor 13 through the adding circuit 10f and the superimposed display control unit 10g. Since the image data $D_H$ applied to the image reversing unit 10c are data of circuit pattern image or others as seen from the bottom of the semiconductor chip of the semiconductor device S, the left-to-right-reversed image data $D_H'$ are data of circuit pattern image (ordinary surface pattern image) as seen from the top of the semiconductor chip of the semiconductor device S and the reproduced image displayed on the color monitor 13 is still picture of ordinary top surface pattern.

Then, the measuring person moves the motor-driven XYZ stage 3 in XY directions while watching the picture (displayed frame by frame) successively displayed on the color monitor 13 to specify the portion of the semiconductor device S to be observed. Further, the measuring person can focus the image by adjusting the height of the motor-driven XYZ stage 3 in Z direction. Furthermore, a clear image from which a noise component and an offset component are removed can be obtained by adjusting the threshold voltage $V_{TH}$ of the contrast intensifying circuit 9h.

Next, in Step (d) of FIG. 6, when the measuring person gives an instruction to start anomalous analysis, the system holds the left-to-right-reversed image data $D_H'$ of one frame stored in the image memory 10e immediately before the instruction, and terminates the fast pickup mode and concurrently switches to the slow pickup mode. In the slow pickup mode, the central processing unit 9a turns off the halogen lump 5a to terminate the illumination of the infrared-ray epi-illumination device 5 (Step (e)) and then the test fixture 7 starts applying an operating voltage to the semiconductor device S and applying a predetermined signal such as an operation.timing clock (step (f)).

Further, the central processing unit 9a sets one frame cycle to 4 seconds and gives a predetermined period within one frame cycle to the shutter driving circuit 2e as an exposure period. Note that the exposure period in the slow pickup mode is longer than that in the fast pickup mode, and cycle of slow point sequential timing is longer than that of fast point sequential timing. That is, the image signal generated in each pixel of the CCD solid state image sensor 2a is read out at slow speed compared with the fast image pickup mode.

Next, in Step (g), the CCD solid image sensor 2a starts taking an image in the slow pickup mode. Then, the shutter device 2c repeats opening and closing for exposure and the CCD solid state image sensor 2a repeats taking image until the slow pickup mode is terminated. Accordingly, the color monitor 13 successively displays still picture every 4 seconds.

The image taking operation in one frame cycle will be described. if there exists some anomaly-occurring portion on the semiconductor chip of the semiconductor device S, the portion will emit very weak light, which will be picked up as an image thereof bv the CCD solid state image sensor 2a. Further, since exposure is made for a long period in the slow pickup mode, a clear image of very weak light is obtained. Then after the predetermined exposure time elapses, the CCD solid state image sensor 2a outputs the image signal $P_L$, synchronizing with the slow point sequential timing, and the slow scanning circuit 9e samples the image signal $P_L$ through the changeover circuit 9g, and the A/D converter 9i converts the image signal $P_L$ into digital image data $D_L$.

Here, one significant point is that since the slow scanning circuit 9e samples and holds every image signal $P_L$ at slow speed in synchronization with the slow point sequential timing, noise of high frequency due to switching when the image is sampled and held can be significantly suppressed and the image signal $P_L'$ with high S/N can be obtained.

Next, thus obtained image data $D_L$ are converted into the left-to-right-reversed image data $D_L'$ in which the arrangement is reversed left to right with respect to the pixel by the image reversing unit 10c, and stored in the image memory 10d. Note that as shown in FIG. 5, the left-to-right-reversed image data $D_L'$ are equivalent to data as seen from the top of the semiconductor chip of the semiconductor device S.

Further, the image memory 10e stores the left-to-right-reversed image data $D_L'$ and at the same time, outputs the left-to-right-reversed image data $D_L'$. The image memory 10d also outputs the left-to-right-reversed image data $D_H'$ with respect to the pixel of the left-to-right-reversed image data $D_L'$. The left-to-right-reversed image data $D_L'$ and the left-to-right-reversed image data $D_H'$ corresponding to each pixel are concurrently supplied to the adding circuit 10f in synchronization with the slow point sequential timing. The adding circuit 10f outputs the superimposed image data $(D_L'+D_H')$, and the superimposed display control unit 10g forms a video signal based on the superimposed image data $(D_L'+D_H')$. In result, the still picture of the image of very weak light showing the anomalous location superimposed on the circuit pattern of the semiconductor device S is displayed on the color monitor 13, and the still picture is switched every four seconds.

Then, when the measuring person gives an instruction to terminate anomalous analysis, the system holds the left-to-right-reversed image data $D_L'$ and the left-to-right-reversed image data $D_H'$, of one frame picture stored in the image memory 10d and the image memory 10e immediately before the instruction, respectively. The still picture of the left-to-right-reversed image data $D_L'$ and the left-to-right-reversed image data $D_H'$ are continuously displayed on the color monitor 13.

As described above, according to the embodiment, the measuring person can observe the anomalous portion easily while watching the display on the color monitor 13.

It should be noted that in the above embodiment, in order to measure the semiconductor device made of silicon semiconductor, the silicon filter is used as an optical filter 5c in the above embodiment, but the present invention is not limited to this. The present invention includes all cases of the optical filter 5c made of the same material as that of the semiconductor device to be measured.

Further, in the embodiment, the cooled CCD camera is used as image pickup means but the present invention is not limited to this. Another kinds of image pickup means can be used. In other words, image pickup means can be an image sensor having sensitivity to the wavelength region including the wavelength region of infrared rays generated using an optical filter made of the same material as that of the semiconductor device to be measured.

Further, in this embodiment, the silicon filter is used as an optical filter in order to measure the image of silicon semiconductor device, but the present invention includes all cases of the optical filter made of the same material as that of the device to be measured. For example, when the image of the GaAs semiconductor device is measured, the optical filter is made of GaAs material.

Thus, according to the present invention described with the embodiments, an image of the semiconductor device to be measured is taken from the bottom and an image of very weak light from the anomalous occurring portion and a pattern image are taken and displayed as a superimposed observed image as if it is observed from the top. Therefore, even though there exists a shielding object such as aluminum wiring, which interrupts light, on the top surface, the anomalous occurring location can be specified. Further, the image of very weak light is converted into the image observed from the top in real time and displayed, so that anomalous occurrence can be analyzed for short period of time. Furthermore, an optical filter made of the same material as that of the semiconductor device to be measured is used to form infrared rays for illumination, so that infrared rays having high transmittance against the semiconductor device can be obtained. As a result of interrupting light having a short wavelength which is easily reflected on the surface of the semiconductor device, a clear reflected optical image which has less noise component and offset component can be taken.

Furthermore, the semiconductor inspection system which can analyze the anomalous occurrence of the semiconductor device at high speed and which is superior in operation and in measurement accuracy, can be provided.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application Nos.286820/1993 filed on Nov. 16, 1994 and 272519/1994 filed on Nov. 7, 1994 are hereby incorporated by reference.

What is claimed is:

1. A system for inspecting a semiconductor device, comprising:
   (A) a dark room box;
   (B) a stage for supporting the semiconductor device, said stage being arranged in said dark room box;
   (C) a test fixture for supplying power to the semiconductor device supported by said stage, wherein weak light is emitted from an anomalous portion in the semiconductor device by supplying power to the semiconductor device;
   (D) a light source for irradiating light onto the semiconductor device supported by said stage;
   (E) a central processing unit for controlling said light source, wherein said light source is turned on in a first period and turned off in a second period;
   (F) an image sensor for detecting a first image of the semiconductor device supported by said stage in the first period, and a second image of the semiconductor device supported by said stage in the second period, wherein the light emitted by said light source and reflected by the semiconductor device is detected by said image sensor as the first image, and wherein the weak light emitted from the anomalous portion of the semiconductor device is detected by said image sensor as the second image;
   (G) an image processing unit for adding data from the first image and data from the second image, said image processing unit being connected to said image sensor;
   (H) a monitor for displaying an image added by said image processing unit; and
   (I) an optical filter arranged in an optical pass way of the light emitted from said light source, said optical filter being comprised of the same material as that of the semiconductor device, said material being one of silicon and Gallium Arsenide.

2. A system according to claim 1, further comprising:
   (a) a fast scanning circuit for reading the data from the first image output from said image sensor;
   (b) a slow scanning circuit for reading the data from the second image output from said image sensor slower than said fast scanning circuit; and
   (c) a changeover circuit for alternatively connecting said image sensor to one of said fast and slow scanning circuits.

3. A system according to claim 1, further comprising:
   (a) a first image memory for storing the data from the first image from said image sensor; and
   (b) a second image memory for storing the data from the second image from said image sensor.

4. A system according to claim 1, wherein both of said optical filter and the semiconductor device are comprised of silicon.

5. A system according to claim 1, further comprising a mouse connected to said image processing unit.

6. A system according to claim 1, further comprising a stage driving unit for controlling operation of said stage.

7. A system for inspecting a semiconductor device, comprising:
   (A) a dark room box;
   (B) a stage for supporting the semiconductor device, said stage being arranged in said dark room box;
   (C) a test fixture for supplying power to the semiconductor device supported by said stage;
   (D) a light source for irradiating light onto the semiconductor device supported by said stage;
   (E) means for controlling said light source;
   (F) an image sensor for detecting a first image of the semiconductor device supported by said stage in a first period, and a second image of the semiconductor device supported by said sage in a second period;
   (G) an image processing unit for adding data from the first image and data from the second image, said image processing unit being connected to said image sensor;
   (H) a monitor for displaying an image added by said image processing unit; and
   (I) an optical filter arranged in an optical pass way of the light emitted from said light source, said optical filter being comprised of the same material as that of the semiconductor device, said material being one of silicon and Gallium Arsenide.

8. A system according to claim 7, further comprising:
   (a) a fast scanning circuit for reading the data from the first image output from said image sensor;
   (b) a slow scanning circuit for reading the data from the second image output from said image sensor slower than said fast scanning circuit; and
   (c) a changeover circuit for alternatively connecting said image sensor to one of said fast and slow scanning circuits.

9. A system according to claim 7 further comprising:
   (a) a first image memory for storing the data from the first image from said image sensor; and
   (b) a second image memory for storing the data from the second image from said image sensor.

10. A system according to claim 7, wherein both of said optical filter and the semiconductor device are comprised of silicon.

11. A system according to claim 7, further comprising a mouse connected to said image processing unit.

12. A system according to claim 7, further comprising a stage driving unit for controlling operation of said stage.

13. A system according to claim 7, wherein said stage is movable.

* * * * *